(12) United States Patent
Baskins (10) Patent No.: US 10,052,282 B2
(45) Date of Patent: Aug. 21, 2018

(54) PET HYDRATION SYSTEM

(71) Applicant: Sydney Baskins, Forestville, MD (US)

(72) Inventor: Sydney Baskins, Forestville, MD (US)

( * ) Notice: Subject to any disclaimer, the term of this patent is extended or adjusted under 35 U.S.C. 154(b) by 153 days.

(21) Appl. No.: 15/274,425

(22) Filed: Sep. 23, 2016

(65) Prior Publication Data
US 2018/0085309 A1  Mar. 29, 2018

(51) Int. Cl.
| | |
|---|---|
| *A01K 5/00* | (2006.01) |
| *A01K 7/00* | (2006.01) |
| *A61K 9/00* | (2006.01) |
| *A61K 33/42* | (2006.01) |
| *A61K 33/06* | (2006.01) |
| *A61K 33/00* | (2006.01) |
| *A61K 33/20* | (2006.01) |
| *A61K 33/26* | (2006.01) |
| *A61K 33/34* | (2006.01) |
| *A61K 33/30* | (2006.01) |
| *A61K 33/32* | (2006.01) |
| *A61K 33/04* | (2006.01) |
| *A61K 33/18* | (2006.01) |
| *A61K 31/375* | (2006.01) |
| *A61K 31/59* | (2006.01) |
| *A61K 31/355* | (2006.01) |
| *A61K 31/122* | (2006.01) |

(Continued)

(52) U.S. Cl.
CPC .......... *A61K 9/0095* (2013.01); *A01K 7/025* (2013.01); *A23K 20/174* (2016.05); *A23K 20/22* (2016.05); *A23K 20/24* (2016.05); *A23K 20/26* (2016.05); *A23K 20/30* (2016.05); *A23K 50/48* (2016.05); *A61K 9/0056* (2013.01); *A61K 31/122* (2013.01); *A61K 31/14* (2013.01); *A61K 31/197* (2013.01); *A61K 31/355* (2013.01); *A61K 31/375* (2013.01); *A61K 31/455* (2013.01); *A61K 31/51* (2013.01); *A61K 31/519* (2013.01); *A61K 31/525* (2013.01); *A61K 31/59* (2013.01); *A61K 31/683* (2013.01); *A61K 31/714* (2013.01); *A61K 33/00* (2013.01); *A61K 33/04* (2013.01); *A61K 33/06* (2013.01); *A61K 33/18* (2013.01); *A61K 33/20* (2013.01); *A61K 33/26* (2013.01); *A61K 33/30* (2013.01); *A61K 33/32* (2013.01); *A61K 33/34* (2013.01); *A61K 33/42* (2013.01); *B65D 1/36* (2013.01)

(58) Field of Classification Search
CPC .............. A61K 2300/00; A61K 9/0095; A23K 20/174; A01K 7/025; A01K 31/122–33/32
USPC ........ 119/74, 710; 426/805, 635, 630, 73, 72
See application file for complete search history.

(56) References Cited

U.S. PATENT DOCUMENTS

| | | | |
|---|---|---|---|
| 2005/0147649 A1* | 7/2005 | Perez-Camargo | ... A61K 31/145 424/442 |
| 2005/0186307 A1* | 8/2005 | Axelrod | ................ A23K 50/40 426/74 |

(Continued)

*Primary Examiner* — Yvonne R Abbott-Lewis
(74) *Attorney, Agent, or Firm* — Michael L. Greenberg, Esq.; Greenberg & Lieberman, LLC (57) ABSTRACT

A pet hydration system comprising of specific ranges of vitamins and minerals conducive to a pet's health, with such nutrients placed into a liquid beverage and ultimately dispensed via a compartmentalized beverage dispenser. The compartmentalized beverage dispenser is formed such that separate liquids are measured out and dispensed to the pet in a manner that the pet receives the optimal amount of nutrition.

19 Claims, 3 Drawing Sheets

(51) Int. Cl.

| | |
|---|---|
| *A61K 31/51* | (2006.01) |
| *A61K 31/525* | (2006.01) |
| *A61K 31/683* | (2006.01) |
| *A61K 31/455* | (2006.01) |
| *A61K 31/197* | (2006.01) |
| *A61K 31/714* | (2006.01) |
| *A61K 31/519* | (2006.01) |
| *A61K 31/14* | (2006.01) |
| *A23K 20/174* | (2016.01) |
| *A23K 20/22* | (2016.01) |
| *A23K 20/24* | (2016.01) |
| *A23K 20/26* | (2016.01) |
| *A23K 20/20* | (2016.01) |
| *A23K 50/48* | (2016.01) |
| *B65D 1/36* | (2006.01) |
| *A01K 7/02* | (2006.01) |

(56) References Cited

U.S. PATENT DOCUMENTS

| | | | |
|---|---|---|---|
| 2006/0193950 A1* | 8/2006 | Axelrod | A23K 40/00 426/74 |
| 2009/0155393 A1* | 6/2009 | Zicker | A61K 8/44 424/736 |
| 2011/0160902 A1* | 6/2011 | Postins | A23K 50/40 700/239 |
| 2016/0310515 A1* | 10/2016 | Singer | A61K 35/20 |
| 2017/0172180 A1* | 6/2017 | Zanghi | A23K 20/147 |
| 2017/0303562 A1* | 10/2017 | Yenichek | A23K 20/10 |
| 2018/0000123 A1* | 1/2018 | Duclos | A23K 20/147 |

* cited by examiner

PET HYDRATION SYSTEM

FIELD OF THE PRESENT INVENTION

The present invention relates to a pet hydration system comprising of specific ranges of vitamins and minerals conducive to a pet's health, with such nutrients placed into a beverage and ultimately dispensed via a compartmentalized beverage dispenser.

BACKGROUND OF THE PRESENT INVENTION

Statistics show that pets often tend to become integral and valued members of the family. This is particularly true for dogs and cats. For example, a study by the American Animal Hospital Association showed that nearly all of the pet owners in the study gave their pet a present at the holidays. In addition, 87 percent of the owners included their pet in holiday celebrations, while 75 percent considered their pet "smart" or "genius." In fact, it was revealed that 63 percent of these owners celebrated the pet's birthday, 43 percent displayed a pet's photograph, and more than half prepared special meals for the pet. These statistics show that owners very much care for the well being of their pets. Moreover, pet owners spend more than $30 billion a year on pet food, services and supplies. All of these statistics add up to the fact that there is a constant need to provide optimal care and comfort for family pets.

Particularly with the expensive nature of veterinary care, there also is a need for combining pet comfort and lifestyle with optimal health care. This is why owners often invest in more expensive premium pet food brands while traditional supermarket brands highly promote nutritional information. It is typically the pet food that provides the most nutritional elements of the pet's diet. However, one aspect of pet care that is perhaps equally vital is the area of pet hydration. Pet owners often want to provide the most ample hydration options to their pets, but at the same time, there is a need to properly have the pet ingest the correct amounts of specific nutrients. This is particularly important due to the nature of pet food and its often filler-like components. In addition, the need extends to the fact that when it comes to bottled water concepts, there must be a means to provide optimal amounts of nutrients relevant to the certain pet physiology, while also providing safeguards that the nutritional intake does not drastically exceed the desired amounts. To this end, the present invention solves this need by including specific ranges of nutrients into a beverage for pets, with such beverage being dispensed to the pet via a compartmentalized beverage dispenser.

U.S. Pat. No. 5,017,389 issued to Green on May 21, 1999 is a nutritional drink composition. Green offers a drink compound for animals that includes percentages of water, dextrose, glycine, electrolytes, and sodium carbonate. Unlike the present invention, Green offers specific ranges of chemicals and nutrients that do not provide optimal vitamins and minerals for certain pets. In addition, Green does not account for the fact that such a beverage can be overdone or underdone in terms of nutritional reliance. In contrast, the present invention provides specific ranges of vitamins and minerals while also providing a means of dispensing the beverage of the present invention in proper and controlled dosages to ensure proper overall care, nutrition and hydration.

U.S. Pat. No. 7,115,297 issued to Stillman on Oct. 31, 2006 is a nutritionally fortified liquid composition with delivery system additives. Stillman offers a drink for humans and pets that is essentially carbonated fiber water. Unlike the present invention, Stillman does not offer specific ranges of vitamins and minerals that are optimal for certain pets. In addition, Stillman does not account for the fact that such a beverage can be overdone or underdone in terms of nutritional reliance. In contrast, the present invention provides specific ranges of vitamins and minerals while also providing a means of dispensing the beverage of the present invention in proper and controlled dosages to ensure proper overall care, nutrition and hydration.

U.S. Pat. No. 4,309,417 issued to Staples on Jan. 5, 1982 is a protein fortified isotonic beverage. Staples provides specific ranges of protein, sodium ion and sweetener as a means for hydration and energy replenishment. Unlike the present invention, Staples does not offer specific ranges of vitamins and minerals that are optimal for certain pets. In addition, Staples does not account for the fact that such a beverage can be overdone or underdone in terms of nutritional reliance. In contrast, the present invention provides specific ranges of vitamins and minerals while also providing a means of dispensing the beverage of the present invention in proper and controlled dosages to ensure proper overall care, nutrition and hydration.

U.S. Pat. No. 6,551,633 issued to Couzy et al on Apr. 22, 2003 is a milk-based powder for pets. Couzy provides a powder comprised of lactose and lactase in such a manner as to help alleviate symptoms of gastrointestinal intolerance. Unlike the present invention, Couzy does not offer specific ranges of vitamins and minerals that are optimal for certain pets and instead relates to cow's milk. In contrast, the present invention provides specific ranges of vitamins and minerals while also providing a means of dispensing the beverage of the present invention in proper and controlled dosages to ensure proper overall care, nutrition and hydration.

U.S. Pat. No. 6,423,360 issued to Lied on Jul. 23, 2002 is a beverage for animals. Lied provides a beverage that has an aromatic substance identical to the smell and enticement of meats and other food combinations that pets may enjoy. Unlike the present invention, Lied does not offer specific ranges of vitamins and minerals that are optimal for certain pets and instead is more of a flavored treat for pets. In contrast, the present invention provides specific ranges of vitamins and minerals while also providing a means of dispensing the beverage of the present invention in proper and controlled dosages to ensure proper overall care, nutrition and hydration.

U.S. Pat. No. 6,613,368 issued to Loti on Sep. 2, 2003 is a dog beverage. Loti employs a tablet that dissolves in water, with the tablet including a meat extract and various other chemicals. Unlike the present invention, Loti does not offer specific ranges of vitamins and minerals that are optimal for certain pets. In addition, Loti does not account for the fact that such a beverage can be overdone or underdone in terms of nutritional reliance. Loti also relies on the tablet which must be dissolved in water. In contrast, the present invention provides specific ranges of vitamins and minerals while also providing a means of dispensing the beverage of the present invention in proper and controlled dosages to ensure proper overall care, nutrition and hydration.

JP 2005102514 filed on Apr. 21, 2005 by Nonoguchi et al is a drinking water for pets. Nonoguchi employs water-soluble edible fiber that serves to inhibit hunger in an effort to control pet obesity. Unlike the present invention, Nonoguchi does not offer specific ranges of vitamins and minerals that are optimal for certain pets and instead focuses on the fiber and hunger inhibiting elements. In contrast, the present invention provides specific ranges of vitamins and minerals while also providing a means of dispensing the beverage of the present invention in proper and controlled dosages to ensure proper overall care, nutrition and hydration.

Other products also have similar shortcoming when it comes to specific ranges of vitamins and minerals that are optimal for certain pets in a vastly different and important manner when relating to the present invention. This includes items such as FORTIFIDO, VITAPAW and K9 WATER CO. products. In addition, these products also fail top prove a dispensing means in regard to proper and controlled dosages to ensure proper overall care, nutrition and hydration. In this regard, the present invention solves the need of optimal vitamins and minerals along with proper hydration, in a manner that dispenses such beverage that is responsible and efficient. Moreover, no other item out there includes the entire composition of vitamins and minerals in the listed amount ranges as the present invention, with these compositions and entirety of nutrients and ranging resulting in optimal nutrition for pets.

SUMMARY OF THE PRESENT INVENTION

The present invention is a pet hydration system. Specific ranges of vitamins and minerals are included into a liquid beverage. This beverage includes these specific ranges of nutrients to cater to household or family pets of various sizes. The beverage in the preferred embodiment of the present invention is placed into a compartmentalized holding container. The holding container is placed on a water bowl that is configured to be compartmentalized and compatible to the compartments of the holding container.

The nutrients of the present invention relate primarily to dogs and cats in regard to the preferred embodiment of the present invention. The ranges of nutrients represent an optimal amount needed for the pet. The nutrients are then included via conventional means into liquid. The liquid is then placed into at least one compartment of the holding container. From there, the owner can dispense as much or as little of the liquid as needed.

DETAILED DESCRIPTION OF THE PREFERRED EMBODIMENT

The present invention includes specific nutrients into a liquid. These nutrients and their amount ranges are necessary to promote optimal health, comfort and longevity of the pet. The type of nutrients and amount ranges are important to achieve the correct amount of health benefits. The ranges and dispensing aspect of the present invention also protects the pet from deficient or excess amounts of malnutrition, both of which can have a negative impact on the pet. Each amount or range of nutritional count pertains to a daily serving for the pet. The proper daily serving relating to such nutritional amounts within the liquid of the present invention is dispensed and controlled via the compartmentalized beverage dispenser.

Calcium of the present invention assists dogs in the formation of bones and teeth, as well as blood coagulation and muscle contraction. In regard to cats, calcium ranges of the present invention prevent skeletal aberrations and maintains bone mineral content. The preferred embodiment of the present invention includes 0.75 g of calcium for average-sized dogs and 0.18 g for average-sized cats.

About 0.75 g of phosphorous for average-sized dogs and 0.16 g for average-sized cats included into the present invention liquid or water assists in skeletal structure and metabolism while maintaining a healthy weight and appetite.

Magnesium is included into the liquid because it contributes to proper enzyme function while also benefiting the mood and longevity of the pet. The optimal amount of magnesium to be included into the present invention is 150 mg for average-sized dogs and 25 mg for average-sized cats.

Sodium is included into the liquid because it contributes to acid-base balance and osmotic pressure regulation in dogs and cats. The optimal amount of sodium to be included into the present invention is 100 mg for average-sized dogs and 42 mg for average-sized cats.

Potassium is included into the liquid because it contributes to acid-base balance and nerve impulse transmission in dogs and cats. The optimal amount of potassium to be included into the present invention is 1 g mg for average-sized dogs and 0.33 g for average-sized cats.

Chlorine is included into the liquid because it contributes to acid-base balance and extracellular fluids across cell membranes in dogs and cats. The optimal amount of chlorine to be included into the present invention is 150 mg for average-sized dogs and 60 mg for average-sized cats.

Iron is included into the liquid because it contributes to synthesis of blood components and energy metabolism in dogs and cats, as well as hemoglobin and myoglobin synthesis in cats. The optimal amount of iron to be included into the present invention is 7.5 mg for average-sized dogs and 5 mg for average-sized cats.

Copper is included into the liquid because it contributes to connective tissue formation and blood cell benefits in dogs and cats. The optimal amount of copper to be included into the present invention is 1.5 mg for average-sized dogs and 0.3 mg for average-sized cats.

Zinc is included into the liquid because it contributes to enzyme reactions and cell replication in dogs and cats. The optimal amount of zinc to be included into the present invention is 15 mg for average-sized dogs and 4.6 mg for average-sized cats.

Manganese is included into the liquid because it contributes to enzyme functions and bone development in dogs and cats. The optimal amount of manganese to be included into the present invention is 1.2 mg for average-sized dogs and 0.3 mg for average-sized cats.

Selenium is included into the liquid because it contributes to defending against oxidative damage in dogs and cats. The optimal amount of selenium to be included into the present invention is 90 micrograms for average-sized dogs and 19 micrograms for average-sized cats.

Iodine is included into the liquid because it contributes to thyroid hormone synthesis and growth in dogs and cats. The optimal amount of iodine to be included into the present invention is 220 micrograms for average-sized dogs and 88 micrograms for average-sized cats.

Vitamin A is included into the liquid because it contributes to vision, growth and immune function in dogs and cats. The optimal amount of vitamin A to be included into the present invention is 379 micrograms for average-sized dogs and 63 micrograms for average-sized cats.

Vitamin D is included into the liquid because it contributes to phosphorous balance in dogs and cats, and skeletal structure in cats. The optimal amount of vitamin D to be included into the present invention is 3.4 micrograms for average-sized dogs and 0.4 micrograms for average-sized cats.

Vitamin E is included into the liquid because it contributes to defense against oxidative damage in dogs and cats. The optimal amount of vitamin E to be included into the present invention is 8 mg for average-sized dogs and 2.5 mg for average-sized cats.

Vitamin K is included into the liquid because it contributes to activation of clotting factors and protein maintenance in dogs and cats. The optimal amount of vitamin K to be included into the present invention is 0.41 mg for average-sized dogs and 82 micrograms for average-sized cats.

Vitamin B1, also referred to as thiamin, is included into the liquid because it contributes to energy and carbohydrate metabolism in dogs and cats, and other neurological benefits in dogs. The optimal amount of vitamin B1 to be included into the present invention is 0.56 mg for average-sized dogs and 0.33 mg for average-sized cats.

Riboflavin is included into the liquid because it contributes to enzyme function in dogs and cats. The optimal amount of riboflavin to be included into the present invention is 1.3 mg for average-sized dogs and 0.27 mg for average-sized cats.

Vitamin B6 is included into the liquid because it contributes to glucose generation and gene, hormone and neurological function in dogs and cats. The optimal amount of vitamin B6 to be included into the present invention is 0.4 mg for average-sized dogs and 0.27 mg for average-sized cats.

Niacin is included into the liquid because it contributes to enzyme function in dogs and cats. The optimal amount of niacin to be included into the present invention is 4 mg for average-sized dogs and 2.5 mg for average-sized cats.

Pantothenic Acid is included into the liquid because it energy metabolism in dogs and cats. The optimal amount of pantothenic acid to be included into the present invention is 4 mg for average-sized dogs and 0.4 mg for average-sized cats.

Vitamin B12 is included into the liquid because it contributes to enzyme function in dogs and cats. The optimal amount of vitamin B12 to be included into the present invention is 9 micrograms for average-sized dogs and 1.4 micrograms for average-sized cats.

Folic acid is included into the liquid because it contributes to amino acid and nucleotide metabolism in dogs and cats. The optimal amount of folic acid to be included into the present invention is 68 micrograms for average-sized dogs and 47 micrograms for average-sized cats.

Choline is included into the liquid because it contributes to the phospholipid cell membrane component in dogs. The optimal amount of choline to be included into the present invention in respect to dogs is 425 mg for average-sized dogs.

The tables below relate to range measurements of minerals and vitamins that are included into daily servings of the present invention. Table 1 relates to the daily range measurements of minerals and vitamins that are served to average sized dogs that consume about 1,000 calories per day. An average sized dog is one that weighs about 33 lbs or 15 kg. Table 2 relates to the daily range measurements of minerals and vitamins that are served to average sized cats that consume about 250 calories per day. An average sized cat is one that weighs about 9 lbs or 4 kg. It is important to note that the ranges in the tables are such that, when used in conjunction with the beverage dispenser, protects dogs and cats from ailments that can occur due to deficient or excess levels of such nutrients.

TABLE 1

| Minerals | |
|---|---|
| Calcium | 0.70-0.80 g |
| Phosphorus | 0.70-0.80 g |
| Magnesium | 140-160 mg |
| Sodium | 90 mg-110 mg |
| Potassium | 0.5-1.5 g |
| Chlorine | 140-160 mg |
| Iron | 7-8 mg |
| Copper | 1-2 mg |
| Zinc | 10-20 mg |
| Manganese | 0.8-1.6 mg |
| Selenium | 80-100 micrograms |
| Iodine | 210-230 micrograms |
| Vitamins | |
| Vitamin A | 360-400 micrograms |
| Vitamin D | 2.9-4.0 micrograms |
| Vitamin E | 4-12 mg |
| Vitamin K | 0.31-0.51 mg |
| Vitamin B1 | 0.49-0.69 mg |
| Riboflavin | .07-2 mg |
| Vitamin B6 | 0.2-0.6 mg |
| Niacin | 2-6 mg |
| Pantothenic Acid | 2-6 mg |
| Vitamin B12 | 6-12 micrograms |
| Folic Acid | 62-75 micrograms |
| Choline | 415-435 mg |

TABLE 2

| Minerals | |
|---|---|
| Calcium | 0.12-0.25 g |
| Phosphorus | 0.10-0.26 g |
| Magnesium | 20-30 mg |
| Sodium | 35 mg-47 mg |
| Potassium | 0.25-39 g |
| Chlorine | 50-70 mg |
| Iron | 3-7 mg |
| Copper | 0.15-0.50 mg |
| Zinc | 4-5.1 mg |
| Manganese | 0.10-0.45 mg |
| Selenium | 12-24 micrograms |
| Iodine | 80-96 micrograms |
| Vitamins | |
| Vitamin A | 55-75 micrograms |
| Vitamin D | 0.2-0.6 micrograms |
| Vitamin E | 2-3 mg |
| Vitamin K | 75-901 mg |
| Vitamin B1 | 0.25-0.40 mg |
| Riboflavin | 0.20-0.35 mg |
| Vitamin B6 | 0.10-0.22 mg |
| Niacin | 2-3 mg |
| Pantothenic Acid | 0.2-0.6 mg |
| Vitamin B12 | 1-2 micrograms |
| Folic Acid | 40-55 micrograms |

Additional embodiments of the present invention are described in Table 3 and Table 4. The optimal ranges of nutritional inclusion in terms of vitamins and minerals within the liquid beverage for average-sized puppies are included in Table 3. The ranges of nutritional inclusion in terms of vitamins and minerals within the liquid beverage for average-sized kittens are included in Table 4.

TABLE 3

| Minerals | |
|---|---|
| Calcium | 0.32-0.40 g |
| Phosphorus | 0.32-0.40 g |
| Magnesium | 70-80 mg |
| Sodium | 45-55 mg |
| Potassium | 0.3-0.7 g |
| Chlorine | 70-80 mg |
| Iron | 3-4.25 mg |
| Copper | 0.25-1.25 mg |
| Zinc | 7-8 mg |
| Manganese | 0.2-0.9 mg |
| Selenium | 40-50 micrograms |
| Iodine | 105-120 micrograms |
| Vitamins | |
| Vitamin A | 185-195 micrograms |
| Vitamin D | 1.2-2.4 micrograms |
| Vitamin E | 2-6 mg |
| Vitamin K | 0.10-0.30 mg |
| Vitamin B1 | 0.20-0.38 mg |
| Riboflavin | 0.35-0.95 mg |
| Vitamin B6 | 0.1-0.4 mg |
| Folic Acid | 30-40 micrograms |
| Choline | 205-220 mg |
| Niacin | 1-3 mg |
| Vitamin B 12 | 3.5-5.5 micrograms |
| Pantothenic Acid | 1-4 mg |

TABLE 4

| Minerals | |
|---|---|
| Calcium | 0.6-0.12 g |
| Phosphorus | 0.5-0.12 g |
| Magnesium | 11-14 mg |
| Sodium | 19-23 mg |
| Potassium | 0.12-0.2 g |
| Chlorine | 25-35 mg |
| Iron | 2-4 mg |
| Copper | 0.1-0.2 mg |
| Zinc | 2-2.7 mg |
| Manganese | 0.1-0.2 mg |
| Selenium | 6-9 micrograms |
| Iodine | 41-46 micrograms |
| Vitamins | |
| Vitamin A | 29-33 pg |
| Vitamin D | 0.1-0.4 pg |
| Vitamin E | 2-4 mg |
| Vitamin K | 80-85 mg |
| Vitamin B1 | 1-2 mg |
| Riboflavin | 0.8-0.18 mg |
| Niacin | 1-2.25 mg |
| Vitamin B 12 | 0.3-1 pg |
| Pantothenic Acid | 0.1-0.4 mg |
| Folic Acid | 20-26 pg |

The nutrients as listed above are included into the liquid via conventional means. That liquid is then poured into the container (10) of the compartmentalized beverage dispenser (5). The compartmentalized beverage dispenser (5) is such that the liquid containing the nutrients as described above is dispensed from the container (10), through the reservoir (20) and out either the first faucet (30) or a second faucet (40). After existing the first faucet (30) or the second faucet (40), the liquid will fall into the tray (50).

Figure 1:
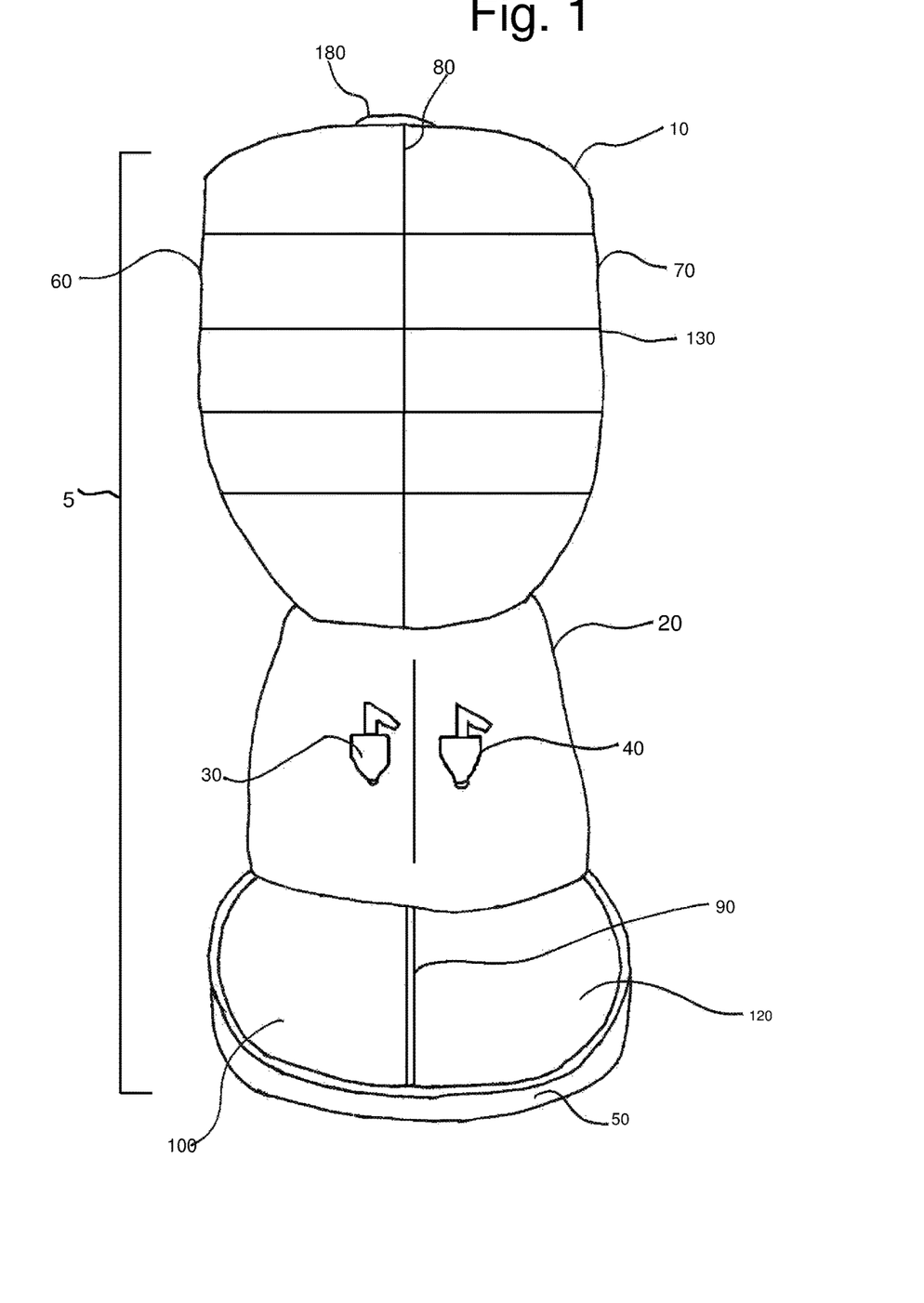
FIG. 1 is a front view of the dispensing element of the present invention.

As can be seen in FIG. 1, the compartmentalized beverage dispenser (5) is divided into at least halves at all points. The container (10) in the preferred embodiment has a left container side (60) and a right container side (70). The container (10) is divided by a container split (80) such that liquid poured into the left container side (60) will not come into contact with the liquid poured into the right container side (70). The container split (80) is formed from conventional material such as waterproof plastic that prevents liquid from passing beyond its borders.

In an additional embodiment of the present invention, water levels are tracked by markings (130), also referred to as grooves, that encompass the container (10) in a longitudinal direction. These markings (130) are such that when the liquid is dispensed, the user can match the top of the liquid level to the next markings (130) to calculate the amount of the liquid to be dispensed. Additionally, a red light (dot) is preferably configured to activate when the present invention detects that the water level is low. The red light is preferably placed on the dispenser. In this manner, the user will not provide too much or too little of the above-mentioned nutritional doses via the liquid. This assists in avoiding improper nutritional intake for the animal. An additional embodiment of the present invention provides measurement numbers listed on the container (10) in their proper formulation. The container split (80) is formed with a conventional sliding mechanism that protrudes out of the container (10). The sliding mechanism has a separate left sliding mechanism and a separate right sliding mechanism that both run from the bottom of the container split (80) to the top of the container split (80). The left sliding mechanism is attached to a left marker that rings around the left container side (60). The right sliding mechanism is attached to a right marker that rings around the right corner side (70). In this manner, a user can effectively move each element of the sliding mechanism in order to cause the markers to move. This permits the user to adjust the markings (130) in order to provide optimal amounts of nutrition from dispensed liquid.

What happens is that a user will empty a first liquid of the present invention into either the left container side (60) or right container side (70) until that particular side of the container (10) is filled to at least one of the grooves (130). The first liquid will include the nutritional ranges as described above, but also may have additional additives such as specific flavoring. Once the first liquid is placed into one of the sides of the container (10), a second liquid will be placed into the container (10) at the opposite side of the container split (80) from where the first liquid was placed. The second liquid may be the same as the first liquid, or it also may be traditional water or another flavor of the liquid of the present invention as described above. The first liquid and/or the second liquid is preferably equipped with one or more flavors to enhance the drinking experience for the pet. The flavors include, but are not limited to, Chicken and Rice flavor, Chicken flavor, Lamb Meal and Rice flavor, Salmon flavor, Liver flavor, Beef flavor, Duck flavor, Tuna flavor, and Vegetarian flavor. The ingredients comprising each of the flavor additives are preferably certified organic in each of the flavors available.

Figure 2:
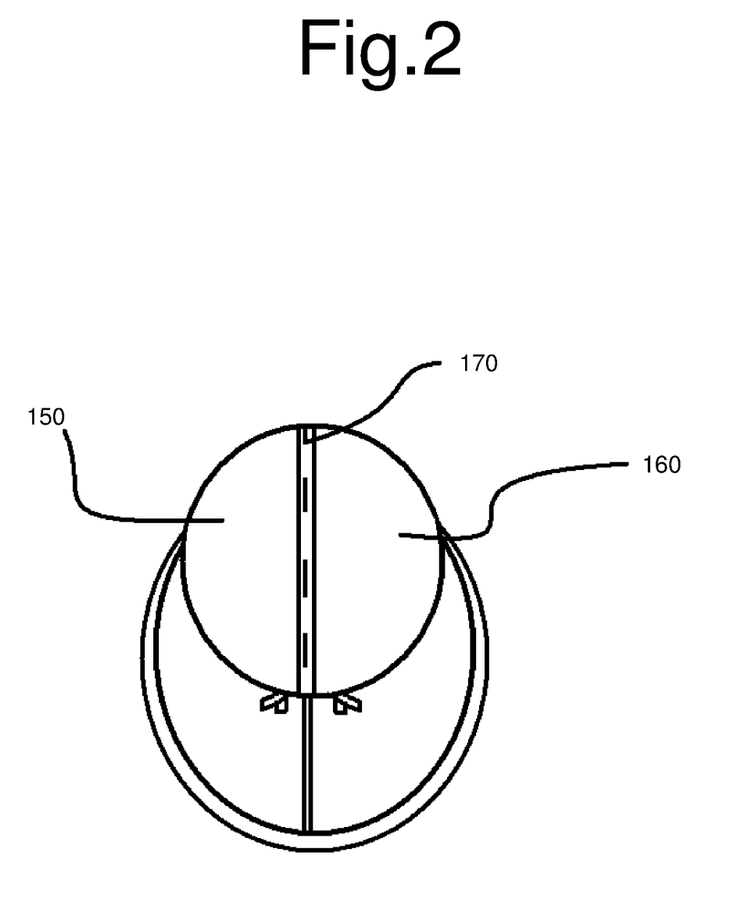
FIG. 2 is a top view of the dispensing element of the present invention.

Once the first liquid and a second liquid are placed into each of the sections of the container (10), specifically the left container side (60) and the right container side (70), activation of the first faucet (30) will cause liquid coming from the left container side (60) via conventional means to pour out of the first faucet (30) via the left reservoir side (150) and into the left tray side (100) of the tray (50). Moreover, activation of the second faucet (40) will cause liquid coming from the right container side (70) via conventional means to pour out of the second faucet (40) via the right reservoir side (160) and into the right tray side (120) of the tray (50). The tray divider (90) serves to segregate the liquids being placed in the left tray side (100) and the right tray side (120). It also should be noted that the reservoir divider (170) serves to maintain separation from the left and right sides of the present invention. In all embodiments of the present invention, it is envisioned that the preferred substrate or base for the first liquid and second liquid is Alkaline water. Alkaline water is preferably used to optimize the health of the pet. Alternate embodiments of the present invention may call for the use of filtered water.

Figure 3:
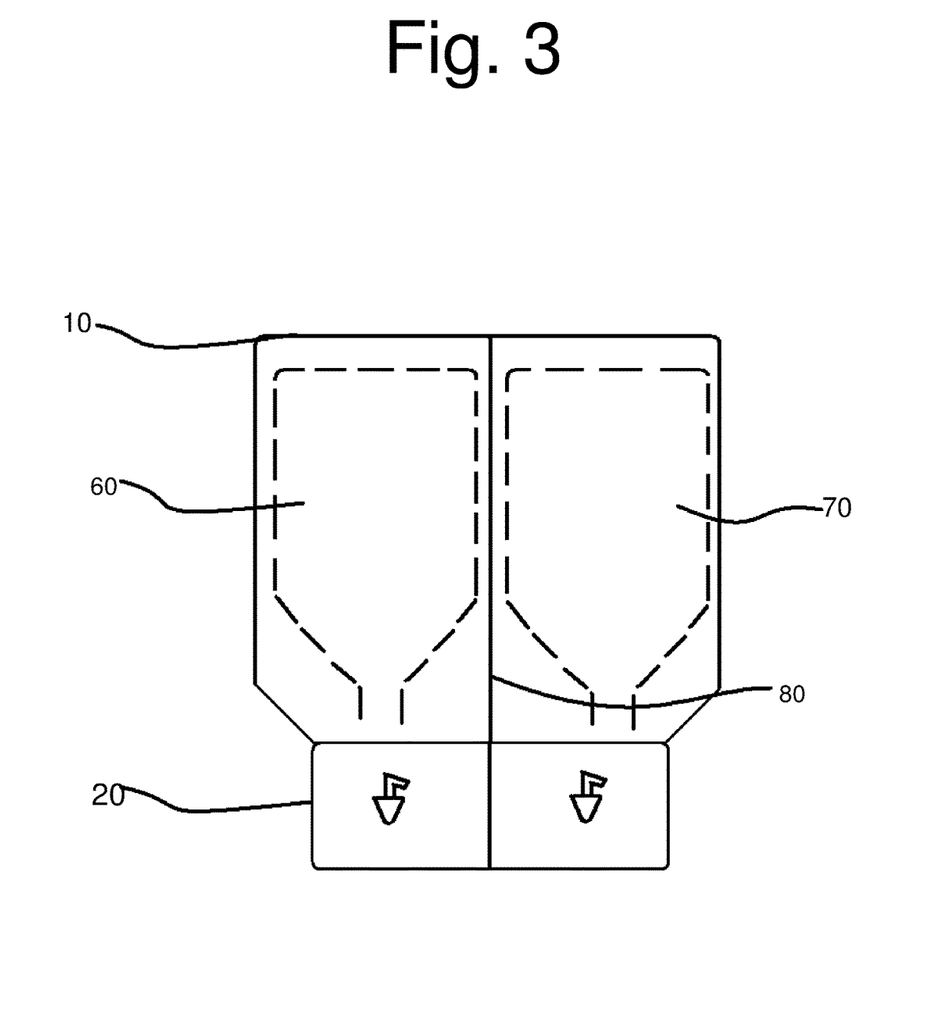
FIG. 3 is a view of an embodiment of the present invention relating to a unitary left container side and a unitary right container side that are both enclosed within the container.

In an additional embodiment of the present invention, as seen in FIG. 3, the left side container (60) and the right side container (70) are each formed as unitary containers placed within the confines of the unitary container (10). The left side container (60) and the right side container (70) are formed such that a thinner opening leads the released liquid into the respective sides of the reservoir (20). In an additional embodiment of FIG. 3, the left side container (60) and right side container (70) are further separated by the container split (80). Both the left side container (60) and the right side container (70) are filled by removing the container (10) via conventional means and pouring the respective liquid into the opening of the left side container (60) and the opening of the right side container (70). The user may then turn the container (10) over and place the container (10) on top of the reservoir (20) such that the container split (80) is aligned and connected to the reservoir divider (170). In addition, the bottom opening of the left container side (60) will line up with the left side of the reservoir (20) and the right container side (70) will line up with the right side of the reservoir (20). An additional embodiment includes a top opening formed and located at the container top (180) of the container (10). This top opening can be snapped or twisted off or otherwise opened via conventional means. Once the top opening is opened, the left container side (60) and the right container side (70) will be exposed at their respective top ends. In this embodiment, another opening that operates via conventional means will be placed at the top end of the left container side (60) and an opening will be placed at the top end of the right container side (70). These openings can be opened and closed via conventional means and are formed such that a user can pour liquid into the opening and then close it up. From there, the user will close the opening at the container top (180).

It should be understood that the present invention may be equipped with a variety of cosmetic embellishments including designs displayed on the left container side (60), right container side (70), and/or container top (180). For example, it is envisioned that pictures of dogs, cats, a sports team logo, or other conventional design may be present on various surfaces of the present invention. Similarly, it is envisioned that the trays holding the water may vary in color and pattern, and may be equipped with glow-in-the-dark plastics, accents, or similar colorations.

Having illustrated the present invention, it should be understood that various adjustments and versions might be implemented without venturing away from the essence of the present invention. Further, it should be understood that the present invention is not solely limited to the invention as described in the embodiments above, but further comprises any and all embodiments within the scope of this application.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

I claim:

1. A pet hydration system, comprising:
mixing minerals into a liquid beverage;
mixing vitamins into the liquid beverage;
mixing calcium into the liquid beverage such that no less than 0.70 g and no more than 0.80 g of the calcium is included into each dispensed dose of the liquid beverage that is dispensed to a dog;
mixing phosphorus into the liquid beverage such that no less than 0.70 g and no more than 0.80 g of the phosphorus is included into each dispensed dose of the liquid beverage that is dispensed to a dog;
mixing magnesium into the liquid beverage such that no less than 140 mg and no more than 160 mg of the magnesium is included into each dispensed dose of the liquid beverage that is dispensed to a dog;
mixing sodium into the liquid beverage such that no less than 90 mg and no more than 110 mg of the sodium is included into each dispensed dose of the liquid beverage that is dispensed to a dog;
mixing potassium into the liquid beverage such that no less than 0.5 g and no more than 1.5 g of the potassium is included into each dispensed dose of the liquid beverage that is dispensed to a dog;
mixing chlorine into the liquid beverage such that no less than 140 mg and no more than 160 mg of the chlorine is included into each dispensed dose of the liquid beverage that is dispensed to a dog;
mixing iron into the liquid beverage such that no less than 7 mg and no more than 8 mg of the iron is included into each dispensed dose of the liquid beverage that is dispensed to a dog;
mixing copper into the liquid beverage such that no less than 1 mg and no more than 2 mg of the copper is included into each dispensed dose of the liquid beverage that is dispensed to a dog;
mixing zinc into the liquid beverage such that no less than 10 mg and no more than 20 mg of the zinc is included into each dispensed dose of the liquid beverage that is dispensed to a dog;
mixing manganese into the liquid beverage such that no less than 0.8 mg and no more than 1.6 mg of the manganese is included into each dispensed dose of the liquid beverage that is dispensed to a dog;
mixing selenium into the liquid beverage such that no less than 80 micrograms and no more than 100 micrograms of the selenium is included into each dispensed dose of the liquid beverage that is dispensed to a dog;
mixing iodine into the liquid beverage such that no less than 210 micrograms and no more than 230 micrograms of the iodine is included into each dispensed dose of the liquid beverage that is dispensed to a dog;
mixing Vitamin A into the liquid beverage such that no less than 360 micrograms and no more than 400 micrograms of the Vitamin A is included into each dispensed dose of the liquid beverage that is dispensed to a dog;
mixing Vitamin D into the liquid beverage such that no less than 2.9 micrograms and no more than 4 micrograms of the Vitamin D is included into each dispensed dose of the liquid beverage that is dispensed to a dog;

mixing Vitamin E into the liquid beverage such that no less than 4 mg and no more than 12 mg of the Vitamin E is included into each dispensed dose of the liquid beverage that is dispensed to a dog;

mixing Vitamin K into the liquid beverage such that no less than 0.31 mg and no more than 0.51 mg of the Vitamin K is included into each dispensed dose of the liquid beverage that is dispensed to a dog;

mixing Vitamin B1 into the liquid beverage such that no less than 0.49 mg and no more than 0.69 mg of the Vitamin B1 is included into each dispensed dose of the liquid beverage that is dispensed to a dog;

mixing riboflavin into the liquid beverage such that no less than 0.07 mg and no more than 2 mg of the riboflavin is included into each dispensed dose of the liquid beverage that is dispensed to a dog;

mixing Vitamin B6 into the liquid beverage such that no less than 0.2 mg and no more than 0.6 mg of the Vitamin B6 is included into each dispensed dose of the liquid beverage that is dispensed to a dog;

mixing niacin into the liquid beverage such that no less than 2 mg and no more than 6 mg of the niacin is included into each dispensed dose of the liquid beverage that is dispensed to a dog;

mixing pantothenic acid into the liquid beverage such that no less than 2 mg and no more than 6 mg of the pantothenic acid is included into each dispensed dose of the liquid beverage that is dispensed to a dog;

mixing Vitamin B12 into the liquid beverage such that no less than 6 micrograms and no more than 12 micrograms of the Vitamin B12 is included into each dispensed dose of the liquid beverage that is dispensed to a dog;

mixing folic acid into the liquid beverage such that no less than 62 micrograms and no more than 75 micrograms of the folic acid is included into each dispensed dose of the liquid beverage that is dispensed to a dog;

mixing choline into the liquid beverage such that no less than 415 mg and no more than 435 mg of the choline is included into each dispensed dose of the liquid beverage that is dispensed to a dog;

mixing calcium into the liquid beverage such that no less than 0.12 g and no more than 0.25 g of the calcium is included into each dispensed dose of the liquid beverage that is dispensed to a cat;

mixing phosphorus into the liquid beverage such that no less than 0.10 g and no more than 0.26 g of the phosphorus is included into each dispensed dose of the liquid beverage that is dispensed to a cat;

mixing magnesium into the liquid beverage such that no less than 20 mg and no more than 30 mg of the magnesium is included into each dispensed dose of the liquid beverage that is dispensed to a cat;

mixing sodium into the liquid beverage such that no less than 35 mg and no more than 47 mg of the sodium is included into each dispensed dose of the liquid beverage that is dispensed to a cat;

mixing potassium into the liquid beverage such that no less than 0.25 and no more than 39 g of the potassium is included into each dispensed dose of the liquid beverage that is dispensed to a cat;

mixing chlorine into the liquid beverage such that no less than 50 mg and no more than 70 mg of the chlorine is included into each dispensed dose of the liquid beverage that is dispensed to a cat;

mixing iron into the liquid beverage such that no less than 3 mg and no more than 7 mg of the iron is included into each dispensed dose of the liquid beverage that is dispensed to a cat;

mixing copper into the liquid beverage such that no less than 0.15 mg and no more than 0.50 mg of the copper is included into each dispensed dose of the liquid beverage that is dispensed to a cat;

mixing zinc into the liquid beverage such that no less than 4 mg and no more than 5.1 mg of the zinc is included into each dispensed dose of the liquid beverage that is dispensed to a cat;

mixing manganese into the liquid beverage such that no less than 0.10 mg and no more than 0.45 mg of the manganese is included into each dispensed dose of the liquid beverage that is dispensed to a cat;

mixing selenium into the liquid beverage such that no less than 12 micrograms and no more than 24 micrograms of the selenium is included into each dispensed dose of the liquid beverage that is dispensed to a cat;

mixing iodine into the liquid beverage such that no less than 80 micrograms and no more than 96 micrograms of the iodine is included into each dispensed dose of the liquid beverage that is dispensed to a cat;

mixing Vitamin A into the liquid beverage such that no less than 55 micrograms and no more than 75 micrograms of the Vitamin A is included into each dispensed dose of the liquid beverage that is dispensed to a cat;

mixing Vitamin D into the liquid beverage such that no less than 0.2 micrograms and no more than 0.6 micrograms of the Vitamin D is included into each dispensed dose of the liquid beverage that is dispensed to a cat;

mixing Vitamin E into the liquid beverage such that no less than 2 mg and no more than 3 mg of the Vitamin E is included into each dispensed dose of the liquid beverage that is dispensed to a cat;

mixing Vitamin K into the liquid beverage such that no less than 75 mg and no more than 901 mg of the Vitamin K is included into each dispensed dose of the liquid beverage that is dispensed to a cat;

mixing Vitamin B1 into the liquid beverage such that no less than 0.25 mg and no more than 0.40 mg of the Vitamin B1 is included into each dispensed dose of the liquid beverage that is dispensed to a cat;

mixing riboflavin into the liquid beverage such that no less than 0.20 mg and no more than 0.35 mg of the riboflavin is included into each dispensed dose of the liquid beverage that is dispensed to a cat;

mixing Vitamin B6 into the liquid beverage such that no less than 0.10 mg and no more than 0.22 mg of the Vitamin B6 is included into each dispensed dose of the liquid beverage that is dispensed to a cat;

mixing niacin into the liquid beverage such that no less than 2 mg and no more than 3 mg of the niacin is included into each dispensed dose of the liquid beverage that is dispensed to a cat;

mixing pantothenic acid into the liquid beverage such that no less than 0.2 mg and no more than 0.6 mg of the pantothenic acid is included into each dispensed dose of the liquid beverage that is dispensed to a cat;

mixing Vitamin B12 into the liquid beverage such that no less than 1 micrograms and no more than 2 micrograms of the Vitamin B12 is included into each dispensed dose of the liquid beverage that is dispensed to a cat; and mixing folic acid into the liquid beverage such that no less than 40 micrograms and no more than 55 micrograms of the folic acid is included into each dispensed dose of the liquid beverage that is dispensed to a cat.

2. The pet hydration system of claim 1, further comprising placing the liquid beverage into a container of a compartmentalized beverage dispenser.

3. The pet hydration system of claim 2, further comprising placing the liquid beverage into the container through a top opening.

4. The pet hydration system of claim 2, further comprising segregating the liquid beverage from a second liquid beverage through use of a container split placed between a left container side and a right container side; and
the container split dividing the liquid beverage from the second liquid beverage such that they do not mix after dispensing.

5. The pet hydration system of claim 2, further comprising forming the compartmentalized beverage dispenser such that the container is placed and removed from a reservoir, the reservoir being secured to a tray.

6. The pet hydration system of claim 5, further comprising dividing the reservoir such that the left container side dispenses the liquid beverage located in the left container side into the left side of the reservoir to be dispensed into a left tray side.

7. The pet hydration system of claim 5, further comprising dividing the reservoir such that the right container side dispenses the liquid beverage located in the right container side into the right side of the reservoir to be dispensed into a right tray side.

8. The pet hydration system of claim 5, further comprising dividing the tray via a tray divider located below and between a left faucet and a right faucet, the left faucet and the right faucet formed with the reservoir.

9. The pet hydration system of claim 2, further comprising forming the container such that the left container side is unitary and the right container side is unitary.

10. The pet hydration system of claim 9, further comprising enclosing the left container side and the right container side with the container.

11. The pet hydration system of claim 2, further comprising placing markings onto the container such that the markings encompass the container in a longitudinal direction.

12. The pet hydration system of claim 11, further comprising calculating dosage levels of the liquid beverage to be dispensed via distances between the markings.

13. The pet hydration system of claim 2, further comprising forming a sliding mechanism into the container split, the sliding mechanism having a separate right sliding mechanism, that is moveable, and a separate left sliding mechanism, that is moveable, that both run from a bottom of the container split to a top of the container split.

14. The pet hydration system of claim 13, further comprising attaching the left sliding mechanism to a left marker of the markings that rings around the left container side such that the markings on the left container side can be adjusted.

15. The pet hydration system of claim 13, further comprising attaching the right sliding mechanism to a right marker of the markings that rings around the right container side such that the markings on the right container side can be adjusted.

16. The pet hydration system of claim 1, further comprising including flavor into the liquid beverage.

17. A pet hydration system, comprising:
mixing minerals into a liquid beverage;
mixing vitamins into the liquid beverage;
mixing calcium into the liquid beverage such that no less than 0.70 g and no more than 0.80 g of the calcium is included into each dispensed dose of the liquid beverage that is dispensed to a dog;
mixing phosphorus into the liquid beverage such that no less than 0.70 g and no more than 0.80 g of the phosphorus is included into each dispensed dose of the liquid beverage that is dispensed to a dog;
mixing magnesium into the liquid beverage such that no less than 140 mg and no more than 160 mg of the magnesium is included into each dispensed dose of the liquid beverage that is dispensed to a dog;
mixing sodium into the liquid beverage such that no less than 90 mg and no more than 110 mg of the sodium is included into each dispensed dose of the liquid beverage that is dispensed to a dog;
mixing potassium into the liquid beverage such that no less than 0.5 g and no more than 1.5 g of the potassium is included into each dispensed dose of the liquid beverage that is dispensed to a dog;
mixing chlorine into the liquid beverage such that no less than 140 mg and no more than 160 mg of the chlorine is included into each dispensed dose of the liquid beverage that is dispensed to a dog;
mixing iron into the liquid beverage such that no less than 7 mg and no more than 8 mg of the iron is included into each dispensed dose of the liquid beverage that is dispensed to a dog;
mixing copper into the liquid beverage such that no less than 1 mg and no more than 2 mg of the copper is included into each dispensed dose of the liquid beverage that is dispensed to a dog;
mixing zinc into the liquid beverage such that no less than 10 mg and no more than 20 mg of the zinc is included into each dispensed dose of the liquid beverage that is dispensed to a dog;
mixing manganese into the liquid beverage such that no less than 0.8 mg and no more than 1.6 mg of the manganese is included into each dispensed dose of the liquid beverage that is dispensed to a dog;
mixing selenium into the liquid beverage such that no less than 80 micrograms and no more than 100 micrograms of the selenium is included into each dispensed dose of the liquid beverage that is dispensed to a dog;
mixing iodine into the liquid beverage such that no less than 210 micrograms and no more than 230 micrograms of the iodine is included into each dispensed dose of the liquid beverage that is dispensed to a dog;
mixing Vitamin A into the liquid beverage such that no less than 360 micrograms and no more than 400 micrograms of the Vitamin A is included into each dispensed dose of the liquid beverage that is dispensed to a dog;
mixing Vitamin D into the liquid beverage such that no less than 2.9 micrograms and no more than 4 micrograms of the Vitamin D is included into each dispensed dose of the liquid beverage that is dispensed to a dog;
mixing Vitamin E into the liquid beverage such that no less than 4 mg and no more than 12 mg of the Vitamin E is included into each dispensed dose of the liquid beverage that is dispensed to a dog;
mixing Vitamin K into the liquid beverage such that no less than 0.31 mg and no more than 0.51 mg of the Vitamin K is included into each dispensed dose of the liquid beverage that is dispensed to a dog;
mixing Vitamin B1 into the liquid beverage such that no less than 0.49 mg and no more than 0.69 mg of the Vitamin B1 is included into each dispensed dose of the liquid beverage that is dispensed to a dog;

mixing riboflavin into the liquid beverage such that no less than 0.07 mg and no more than 2 mg of the riboflavin is included into each dispensed dose of the liquid beverage that is dispensed to a dog;

mixing Vitamin B6 into the liquid beverage such that no less than 0.2 mg and no more than 0.6 mg of the Vitamin B6 is included into each dispensed dose of the liquid beverage that is dispensed to a dog;

mixing niacin into the liquid beverage such that no less than 2 mg and no more than 6 mg of the niacin is included into each dispensed dose of the liquid beverage that is dispensed to a dog;

mixing pantothenic acid into the liquid beverage such that no less than 2 mg and no more than 6 mg of the pantothenic acid is included into each dispensed dose of the liquid beverage that is dispensed to a dog;

mixing Vitamin B12 into the liquid beverage such that no less than 6 micrograms and no more than 12 micrograms of the Vitamin B12 is included into each dispensed dose of the liquid beverage that is dispensed to a dog;

mixing folic acid into the liquid beverage such that no less than 62 micrograms and no more than 75 micrograms of the folic acid is included into each dispensed dose of the liquid beverage that is dispensed to a dog;

mixing choline into the liquid beverage such that no less than 415 mg and no more than 435 mg of the choline is included into each dispensed dose of the liquid beverage that is dispensed to a dog;

mixing calcium into the liquid beverage such that no less than 0.12 g and no more than 0.25 g of the calcium is included into each dispensed dose of the liquid beverage that is dispensed to a cat;

mixing phosphorus into the liquid beverage such that no less than 0.10 g and no more than 0.26 g of the phosphorus is included into each dispensed dose of the liquid beverage that is dispensed to a cat;

mixing magnesium into the liquid beverage such that no less than 20 mg and no more than 30 mg of the magnesium is included into each dispensed dose of the liquid beverage that is dispensed to a cat;

mixing sodium into the liquid beverage such that no less than 35 mg and no more than 47 mg of the sodium is included into each dispensed dose of the liquid beverage that is dispensed to a cat;

mixing potassium into the liquid beverage such that no less than 0.25 and no more than 39 g of the potassium is included into each dispensed dose of the liquid beverage that is dispensed to a cat;

mixing chlorine into the liquid beverage such that no less than 50 mg and no more than 70 mg of the chlorine is included into each dispensed dose of the liquid beverage that is dispensed to a cat;

mixing iron into the liquid beverage such that no less than 3 mg and no more than 7 mg of the iron is included into each dispensed dose of the liquid beverage that is dispensed to a cat;

mixing copper into the liquid beverage such that no less than 0.15 mg and no more than 0.50 mg of the copper is included into each dispensed dose of the liquid beverage that is dispensed to a cat;

mixing zinc into the liquid beverage such that no less than 4 mg and no more than 5.1 mg of the zinc is included into each dispensed dose of the liquid beverage that is dispensed to a cat;

mixing manganese into the liquid beverage such that no less than 0.10 mg and no more than 0.45 mg of the manganese is included into each dispensed dose of the liquid beverage that is dispensed to a cat;

mixing selenium into the liquid beverage such that no less than 12 micrograms and no more than 24 micrograms of the selenium is included into each dispensed dose of the liquid beverage that is dispensed to a cat;

mixing iodine into the liquid beverage such that no less than 80 micrograms and no more than 96 micrograms of the iodine is included into each dispensed dose of the liquid beverage that is dispensed to a cat;

mixing Vitamin A into the liquid beverage such that no less than 55 micrograms and no more than 75 micrograms of the Vitamin A is included into each dispensed dose of the liquid beverage that is dispensed to a cat;

mixing Vitamin D into the liquid beverage such that no less than 0.2 micrograms and no more than 0.6 micrograms of the Vitamin D is included into each dispensed dose of the liquid beverage that is dispensed to a cat;

mixing Vitamin E into the liquid beverage such that no less than 2 mg and no more than 3 mg of the Vitamin E is included into each dispensed dose of the liquid beverage that is dispensed to a cat;

mixing Vitamin K into the liquid beverage such that no less than 75 mg and no more than 901 mg of the Vitamin K is included into each dispensed dose of the liquid beverage that is dispensed to a cat;

mixing Vitamin B1 into the liquid beverage such that no less than 0.25 mg and no more than 0.40 mg of the Vitamin B1 is included into each dispensed dose of the liquid beverage that is dispensed to a cat;

mixing riboflavin into the liquid beverage such that no less than 0.20 mg and no more than 0.35 mg of the riboflavin is included into each dispensed dose of the liquid beverage that is dispensed to a cat;

mixing Vitamin B6 into the liquid beverage such that no less than 0.10 mg and no more than 0.22 mg of the Vitamin B6 is included into each dispensed dose of the liquid beverage that is dispensed to a cat;

mixing niacin into the liquid beverage such that no less than 2 mg and no more than 3 mg of the niacin is included into each dispensed dose of the liquid beverage that is dispensed to a cat;

mixing pantothenic acid into the liquid beverage such that no less than 0.2 mg and no more than 0.6 mg of the pantothenic acid is included into each dispensed dose of the liquid beverage that is dispensed to a cat;

mixing Vitamin B12 into the liquid beverage such that no less than 1 micrograms and no more than 2 micrograms of the Vitamin B12 is included into each dispensed dose of the liquid beverage that is dispensed to a cat;

mixing folic acid into the liquid beverage such that no less than 40 micrograms and no more than 55 micrograms of the folic acid is included into each dispensed dose of the liquid beverage that is dispensed to a cat;

further comprising placing the liquid beverage into a container of a compartmentalized beverage dispenser;

further comprising placing the liquid beverage into the container through a top opening;

further comprising segregating the liquid beverage from a second liquid beverage through use of a container split placed between a left container side and a right container side;

further comprising forming the compartmentalized beverage dispenser such that the container is placed and removed from a reservoir, the reservoir being secured to a tray;

further comprising dividing the reservoir such that the left container side dispenses the liquid beverage located in the left container side into the left side of the reservoir to be dispensed into a left tray side;

further comprising dividing the reservoir such that the right container side dispenses the liquid beverage located in the right container side into the right side of the reservoir to be dispensed into a right tray side;

further comprising dividing the tray via a tray divider located below and between a left faucet and a right faucet, the left faucet and the right faucet formed with the reservoir;

further comprising forming the container such that the left container side is unitary and the right container side is unitary;

further comprising enclosing the left container side and the right container side with the container;

further comprising placing markings onto the container such that the markings encompass the container in a longitudinal direction;

further comprising calculating dosage levels of the liquid beverage to be dispensed via distances between the markings;

further comprising forming a sliding mechanism into the container split, the sliding mechanism having a separate right sliding mechanism, that is moveable, and a separate left sliding mechanism, that is moveable, that both run from a bottom of the container split to a top of the container split;

further comprising attaching the left sliding mechanism to a left marker of the markings that rings around the left container side such that the markings on the left container side can be adjusted;

further comprising attaching the right sliding mechanism to a right marker of the markings that rings around the right container side such that the markings on the right container side can be adjusted; and further comprising including flavor into the liquid beverage.

18. A pet hydration system, comprising:

mixing minerals into a liquid beverage;

mixing vitamins into the liquid beverage;

mixing calcium into the liquid beverage such that no less than 0.32 g and no more than 0.40 g of the calcium is included into each dispensed dose of the liquid beverage that is dispensed to a dog;

mixing phosphorus into the liquid beverage such that no less than 0.32 g and no more than 0.40 g of the phosphorus is included into each dispensed dose of the liquid beverage that is dispensed to a dog;

mixing magnesium into the liquid beverage such that no less than 70 mg and no more than 80 mg of the magnesium is included into each dispensed dose of the liquid beverage that is dispensed to a dog;

mixing sodium into the liquid beverage such that no less than 45 mg and no more than 55 mg of the sodium is included into each dispensed dose of the liquid beverage that is dispensed to a dog;

mixing potassium into the liquid beverage such that no less than 0.3 g and no more than 0.7 g of the potassium is included into each dispensed dose of the liquid beverage that is dispensed to a dog;

mixing chlorine into the liquid beverage such that no less than 70 mg and no more than 80 mg of the chlorine is included into each dispensed dose of the liquid beverage that is dispensed to a dog;

mixing iron into the liquid beverage such that no less than 3 mg and no more than 4.25 mg of the iron is included into each dispensed dose of the liquid beverage that is dispensed to a dog;

mixing copper into the liquid beverage such that no less than 0.25 mg and no more than 1.25 mg of the copper is included into each dispensed dose of the liquid beverage that is dispensed to a dog;

mixing zinc into the liquid beverage such that no less than 7 mg and no more than 8 mg of the zinc is included into each dispensed dose of the liquid beverage that is dispensed to a dog;

mixing manganese into the liquid beverage such that no less than 0.2 mg and no more than 0.9 mg of the manganese is included into each dispensed dose of the liquid beverage that is dispensed to a dog;

mixing selenium into the liquid beverage such that no less than 40 micrograms and no more than 50 micrograms of the selenium is included into each dispensed dose of the liquid beverage that is dispensed to a dog;

mixing iodine into the liquid beverage such that no less than 105 micrograms and no more than 120 micrograms of the iodine is included into each dispensed dose of the liquid beverage that is dispensed to a dog;

mixing Vitamin A into the liquid beverage such that no less than 185 micrograms and no more than 195 micrograms of the Vitamin A is included into each dispensed dose of the liquid beverage that is dispensed to a dog;

mixing Vitamin D into the liquid beverage such that no less than 1.2 micrograms and no more than 2.4 micrograms of the Vitamin D is included into each dispensed dose of the liquid beverage that is dispensed to a dog;

mixing Vitamin E into the liquid beverage such that no less than 2 mg and no more than 6 mg of the Vitamin E is included into each dispensed dose of the liquid beverage that is dispensed to a dog;

mixing Vitamin K into the liquid beverage such that no less than 0.10 mg and no more than 0.30 mg of the Vitamin K is included into each dispensed dose of the liquid beverage that is dispensed to a dog;

mixing Vitamin B1 into the liquid beverage such that no less than 0.20 mg and no more than 0.38 mg of the Vitamin B1 is included into each dispensed dose of the liquid beverage that is dispensed to a dog;

mixing riboflavin into the liquid beverage such that no less than 0.35 mg and no more than 0.95 mg of the riboflavin is included into each dispensed dose of the liquid beverage that is dispensed to a dog;

mixing Vitamin B6 into the liquid beverage such that no less than 0.1 mg and no more than 0.4 mg of the Vitamin B6 is included into each dispensed dose of the liquid beverage that is dispensed to a dog;

mixing niacin into the liquid beverage such that no less than 1 mg and no more than 3 mg of the niacin is included into each dispensed dose of the liquid beverage that is dispensed to a dog;

mixing pantothenic acid into the liquid beverage such that no less than 1 mg and no more than 4 mg of the pantothenic acid is included into each dispensed dose of the liquid beverage that is dispensed to a dog;

mixing Vitamin B12 into the liquid beverage such that no less than 3.5 micrograms and no more than 5.5 micrograms of the Vitamin B12 is included into each dispensed dose of the liquid beverage that is dispensed to a dog;

mixing folic acid into the liquid beverage such that no less than 30 micrograms and no more than 40 micrograms of the folic acid is included into each dispensed dose of the liquid beverage that is dispensed to a dog;

mixing choline into the liquid beverage such that no less than 205 mg and no more than 220 mg of the choline is included into each dispensed dose of the liquid beverage that is dispensed to a dog;

mixing calcium into the liquid beverage such that no less than 0.6 g and no more than 0.12 g of the calcium is included into each dispensed dose of the liquid beverage that is dispensed to a cat;

mixing phosphorus into the liquid beverage such that no less than 0.5 g and no more than 0.12 g of the phosphorus is included into each dispensed dose of the liquid beverage that is dispensed to a cat;

mixing magnesium into the liquid beverage such that no less than 11 mg and no more than 14 mg of the magnesium is included into each dispensed dose of the liquid beverage that is dispensed to a cat;

mixing sodium into the liquid beverage such that no less than 19 mg and no more than 23 mg of the sodium is included into each dispensed dose of the liquid beverage that is dispensed to a cat;

mixing potassium into the liquid beverage such that no less than 0.12 and no more than 0.2 g of the potassium is included into each dispensed dose of the liquid beverage that is dispensed to a cat;

mixing chlorine into the liquid beverage such that no less than 25 mg and no more than 35 mg of the chlorine is included into each dispensed dose of the liquid beverage that is dispensed to a cat;

mixing iron into the liquid beverage such that no less than 2 mg and no more than 4 mg of the iron is included into each dispensed dose of the liquid beverage that is dispensed to a cat;

mixing copper into the liquid beverage such that no less than 0.1 mg and no more than 0.2 mg of the copper is included into each dispensed dose of the liquid beverage that is dispensed to a cat;

mixing zinc into the liquid beverage such that no less than 2 mg and no more than 2.7 mg of the zinc is included into each dispensed dose of the liquid beverage that is dispensed to a cat;

mixing manganese into the liquid beverage such that no less than 0.10 mg and no more than 0.20 mg of the manganese is included into each dispensed dose of the liquid beverage that is dispensed to a cat;

mixing selenium into the liquid beverage such that no less than 6 micrograms and no more than 9 micrograms of the selenium is included into each dispensed dose of the liquid beverage that is dispensed to a cat;

mixing iodine into the liquid beverage such that no less than 41 micrograms and no more than 46 micrograms of the iodine is included into each dispensed dose of the liquid beverage that is dispensed to a cat;

mixing Vitamin A into the liquid beverage such that no less than 29 micrograms and no more than 33 micrograms of the Vitamin A is included into each dispensed dose of the liquid beverage that is dispensed to a cat;

mixing Vitamin D into the liquid beverage such that no less than 0.1 micrograms and no more than 0.4 micrograms of the Vitamin D is included into each dispensed dose of the liquid beverage that is dispensed to a cat;

mixing Vitamin E into the liquid beverage such that no less than 2 mg and no more than 4 mg of the Vitamin E is included into each dispensed dose of the liquid beverage that is dispensed to a cat;

mixing Vitamin K into the liquid beverage such that no less than 80 mg and no more than 85 mg of the Vitamin K is included into each dispensed dose of the liquid beverage that is dispensed to a cat;

mixing Vitamin B1 into the liquid beverage such that no less than 1 mg and no more than 2 mg of the Vitamin B1 is included into each dispensed dose of the liquid beverage that is dispensed to a cat;

mixing riboflavin into the liquid beverage such that no less than 0.8 mg and no more than 0.18 mg of the riboflavin is included into each dispensed dose of the liquid beverage that is dispensed to a cat;

mixing niacin into the liquid beverage such that no less than 1 mg and no more than 2.25 mg of the niacin is included into each dispensed dose of the liquid beverage that is dispensed to a cat;

mixing pantothenic acid into the liquid beverage such that no less than 0.1 mg and no more than 0.4 mg of the pantothenic acid is included into each dispensed dose of the liquid beverage that is dispensed to a cat;

mixing Vitamin B12 into the liquid beverage such that no less than 0.3 micrograms and no more than 1 micrograms of the Vitamin B12 is included into each dispensed dose of the liquid beverage that is dispensed to a cat;

mixing folic acid into the liquid beverage such that no less than 20 micrograms and no more than 26 micrograms of the folic acid is included into each dispensed dose of the liquid beverage that is dispensed to a cat;

further comprising placing the liquid beverage into a container of a compartmentalized beverage dispenser;

further comprising placing the liquid beverage into the container through a top opening;

further comprising segregating the liquid beverage from a second liquid beverage through use of a container split placed between a left container side and a right container side;

further comprising forming the compartmentalized beverage dispenser such that the container is placed and removed from a reservoir, the reservoir being secured to a tray;

further comprising dividing the reservoir such that the left container side dispenses the liquid beverage located in the left container side into the left side of the reservoir to be dispensed into a left tray side;

further comprising dividing the reservoir such that the right container side dispenses the liquid beverage located in the right container side into the right side of the reservoir to be dispensed into a right tray side;

further comprising dividing the tray via a tray divider located below and between a left faucet and a right faucet, the left faucet and the right faucet formed with the reservoir;

further comprising forming the container such that the left container side is unitary and the right container side is unitary;

further comprising enclosing the left container side and the right container side with the container;

further comprising placing markings onto the container such that the markings encompass the container in a longitudinal direction;

further comprising calculating dosage levels of the liquid beverage to be dispensed via distances between the markings;

further comprising forming a sliding mechanism into the container split, the sliding mechanism having a separate right sliding mechanism, that is moveable, and a separate left sliding mechanism, that is moveable, that both run from a bottom of the container split to a top of the container split;

further comprising attaching the left sliding mechanism to a left marker of the markings that rings around the left container side such that the markings on the left container side can be adjusted;

further comprising attaching the right sliding mechanism to a right marker of the markings that rings around the right container side such that the markings on the right container side can be adjusted; and further comprising including flavor into the liquid beverage.

19. The method of claim 18, wherein said 'mixing minerals into a liquid beverage,' and said 'mixing vitamins into the liquid beverage' are premixed; and wherein the minerals and the vitamins are prepackaged.

\* \* \* \* \*